United States Patent
Sud et al.

(10) Patent No.: US 12,053,301 B2
(45) Date of Patent: Aug. 6, 2024

(54) CLASSIFYING FACIAL EXPRESSIONS USING EYE-TRACKING CAMERAS

(71) Applicant: Google LLC, Mountain View, CA (US)

(72) Inventors: Avneesh Sud, Mountain View, CA (US); Steven Hickson, Mountain View, CA (US); Vivek Kwatra, Bangalore (IN); Nicholas Dufour, Mountain View, CA (US)

(73) Assignee: GOOGLE LLC, Mountain View, CA (US)

( * ) Notice: Subject to any disclaimer, the term of this patent is extended or adjusted under 35 U.S.C. 154(b) by 469 days.

(21) Appl. No.: 17/339,128

(22) Filed: Jun. 4, 2021

(65) Prior Publication Data
US 2021/0295025 A1 Sep. 23, 2021

Related U.S. Application Data

(62) Division of application No. 15/831,823, filed on Dec. 5, 2017, now Pat. No. 11,042,729.

(Continued)

(51) Int. Cl.
*A61B 5/00* (2006.01)
*A61B 5/16* (2006.01)
(Continued)

(52) U.S. Cl.
CPC ............ *A61B 5/6803* (2013.01); *A61B 5/165* (2013.01); *G01S 3/00* (2013.01); *G06F 3/013* (2013.01);
(Continued)

(58) Field of Classification Search
None
See application file for complete search history.

(56) References Cited

U.S. PATENT DOCUMENTS 11,042,729 B2 * 6/2021 Sud .................... G06F 3/013
2016/0341959 A1 11/2016 Gibbs et al.
(Continued)

FOREIGN PATENT DOCUMENTS

WO WO-2015167909 A1 * 11/2015 ........... A63F 13/212

OTHER PUBLICATIONS

Ghosh et al. ("A multi-label convolutional neural network approach to cross-domain action unit detection." 2015 International Conference on Affective Computing and Intelligent Interaction (ACII). IEEE, 2015.) (Year: 2015).*

(Continued)

*Primary Examiner* — Randolph I Chu

(57) ABSTRACT

Images of a plurality of users are captured concurrently with the plurality of users evincing a plurality of expressions. The images are captured using one or more eye tracking sensors implemented in one or more head mounted devices (HMDs) worn by the plurality of first users. A machine learnt algorithm is trained to infer labels indicative of expressions of the users in the images. A live image of a user is captured using an eye tracking sensor implemented in an HMD worn by the user. A label of an expression evinced by the user in the live image is inferred using the machine learnt algorithm that has been trained to predict labels indicative of expressions. The images of the users and the live image can be personalized by combining the images with personalization images of the users evincing a subset of the expressions.

20 Claims, 7 Drawing Sheets

Related U.S. Application Data

(60) Provisional application No. 62/492,861, filed on May 1, 2017.

(51) Int. Cl.

| | | |
|---|---|---|
| *G01S 3/00* | (2006.01) | |
| *G06F 3/01* | (2006.01) | |
| *G06F 18/214* | (2023.01) | |
| *G06F 18/2413* | (2023.01) | |
| *G06N 3/04* | (2023.01) | |
| *G06N 3/045* | (2023.01) | |
| *G06N 3/08* | (2023.01) | |
| *G06V 10/44* | (2022.01) | |
| *G06V 10/764* | (2022.01) | |
| *G06V 10/82* | (2022.01) | |
| *G06V 20/20* | (2022.01) | |
| *G06V 40/16* | (2022.01) | |
| *H04N 23/60* | (2023.01) | |
| *H04N 23/611* | (2023.01) | |
| *G06V 40/19* | (2022.01) | |
| *H04N 13/344* | (2018.01) | |

(52) U.S. Cl.
 CPC ........ *G06F 18/214* (2023.01); *G06F 18/2413* (2023.01); *G06N 3/04* (2013.01); *G06N 3/045* (2023.01); *G06N 3/08* (2013.01); *G06V 10/454* (2022.01); *G06V 10/764* (2022.01); *G06V 10/82* (2022.01); *G06V 20/20* (2022.01); *G06V 40/174* (2022.01); *H04N 23/60* (2023.01); *H04N 23/611* (2023.01); *A61B 5/163* (2017.08); *A61B 5/7267* (2013.01); *A61B 5/7275* (2013.01); *G06V 40/19* (2022.01); *H04N 13/344* (2018.05)

(56) References Cited

U.S. PATENT DOCUMENTS

| | | | |
|---|---|---|---|
| 2016/0343164 A1* | 11/2016 | Urbach | G02B 27/017 |
| 2016/0360970 A1* | 12/2016 | Tzvieli | A61B 5/0075 |
| 2017/0103440 A1* | 4/2017 | Xing | H04W 12/06 |
| 2017/0285732 A1* | 10/2017 | Daly | A61B 5/0205 |
| 2017/0344812 A1* | 11/2017 | Kim | G06V 40/174 |
| 2018/0082482 A1* | 3/2018 | Motta | G06F 3/012 |
| 2021/0007607 A1* | 1/2021 | Frank | A61B 5/14552 |
| 2021/0295025 A1* | 9/2021 | Sud | G06F 1/163 |
| 2023/0040793 A1* | 2/2023 | Sud | G06V 20/647 |

OTHER PUBLICATIONS

Kapoor et al. ("Fully automatic upper facial action recognition", Analysis and Modeling of Faces and Gestures, 2003. AMFG 2003. IEEE International Workshop On, Oct. 17, 2003). (Year: 2003).*
PCT Written Opinion of the international Searching Authority for PCT/US2018/017592 (Year: 2018).*
European Office Action mailed May 26, 2021 for EP Application No. 18707479.4, 6 pages.
Translation of Chinese Office Action mailed Sep. 29, 2022 for CN Application No. 201880009128.0, 27 pages.
Translation of Chinese Notification on the Grant of Patent Right for Invention mailed Mar. 28, 2023, for CN Application No. 201880009128. 0, 4 pages.

* cited by examiner

CLASSIFYING FACIAL EXPRESSIONS USING EYE-TRACKING CAMERAS

CROSS-REFERENCE TO RELATED APPLICATIONS

The present application is a divisional application of U.S. patent application Ser. No. 15/831,823, entitled "Classifying Facial Expressions Using Eye-Tracking Cameras" and filed on Dec. 5, 2017, the entirety of which is incorporated by reference herein.

BACKGROUND

Immersive virtual reality (VR), augmented reality (AR), or mixed reality (MR) systems typically utilize a head mounted display (HMD) that presents stereoscopic imagery to the user so as to give a sense of presence in a three-dimensional (3D) scene. A typical HMD is designed to produce a stereoscopic image over a field-of-view that approaches or is equal to the field-of-view of a human eye, which is approximately 180°. For example, the field-of-view of commercial HMDs is currently 100-110°. Multiple users can interact with each other in the same 3-D scene produced by an immersive VR, AR, or MR system. For example, users can interact with each other using 3D video conferencing, while co-watching movies or YouTube videos in a virtual theater, taking a virtual hike through a region in Google Earth, or while sitting in a virtual 3D classroom listening to a lecture by a (real or virtual) professor. Users in a 3-D scene can be represented using captured images of the user or avatars that represent the user. For example, immersive VR, AR, or MR systems can use a camera to capture images of the users, which are then inserted into the virtual 3-D scene. For another example, an avatar that represents the user can be inserted into the virtual 3-D scene. In either case, facial expressions are not easily conveyed by the representation of the user. The HMD occludes a large portion of the user's face that includes the user's eyes, which makes it difficult to convey emotion in captured images of the user, and the expression on the face of an avatar does not typically convey the actual emotional state of the corresponding user. Occlusion by the HMD also limits the possibilities for evaluating the response of the user to the VR content.

BRIEF DESCRIPTION OF THE DRAWINGS

The present disclosure may be better understood, and its numerous features and advantages made apparent to those skilled in the art by referencing the accompanying drawings. The use of the same reference symbols in different drawings indicates similar or identical items.

DETAILED DESCRIPTION

Figure 1:
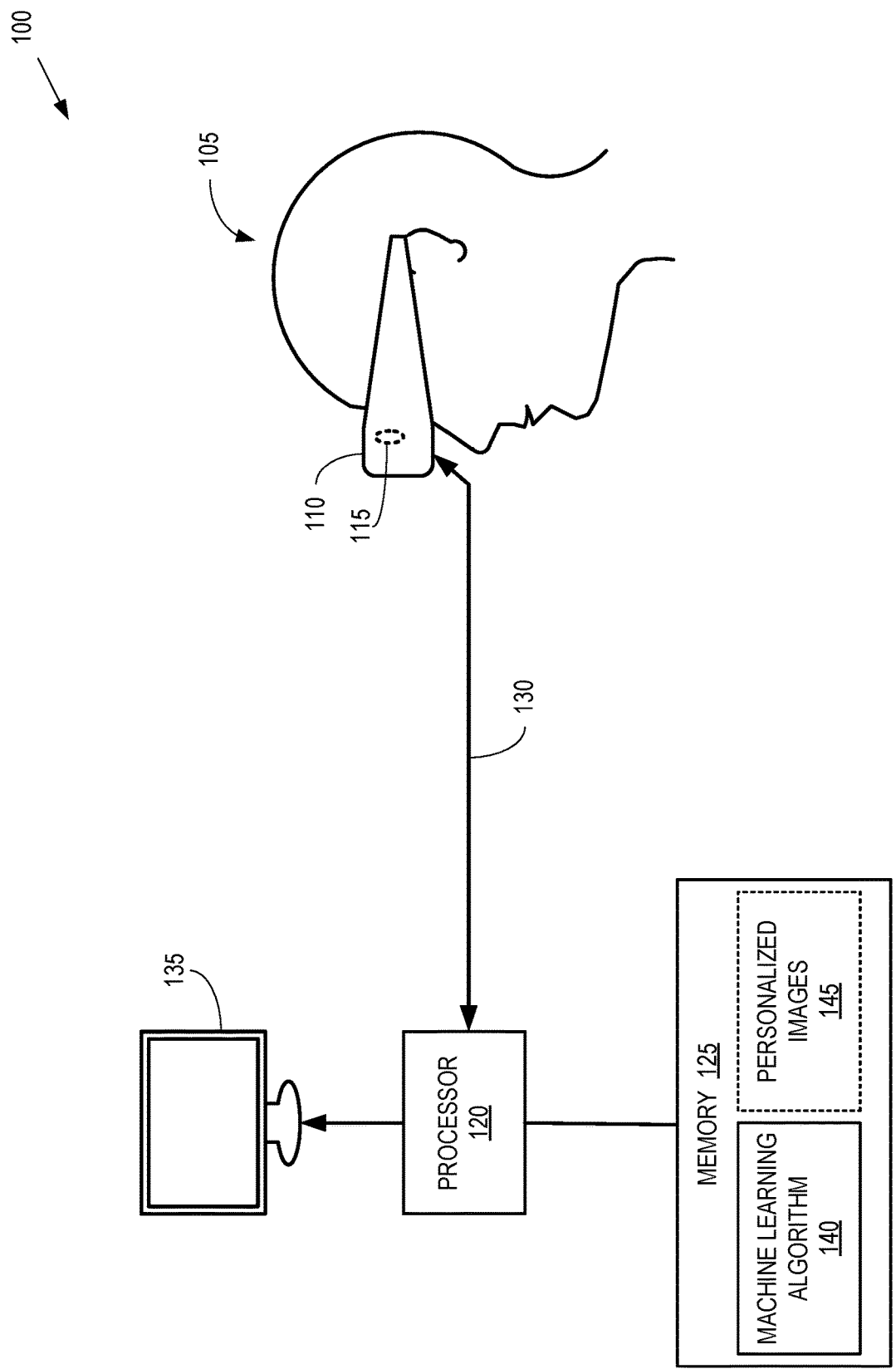
FIG. 1 is a diagram illustrating a processing system that is configured to infer labels of emotions corresponding to facial expressions of the user according to some embodiments.

A processing system can infer user expressions from unoccluded frontal images of the user's face. Some embodiments of the processing system can implement feature tracking and neural network algorithms to detect values of parameters that indicate facial deformations, such as action units that indicate states of muscle contraction in independent muscle groups on the user's face. For example, a user's facial expression can be characterized by values of approximately 46 facial action units distributed around the face. Occluding the user's face with an HMD significantly complicates the task of inferring user expressions based on images of the user wearing the HMD. Several action unit muscle groups are in the region of the user's face that would be occluded by an HMD and the occluded action units include key indicators of emotion such as eyebrow raises, cheek raises, winks, and squints. Specialized optical or piezoelectric sensors can be incorporated into an HMD and use to track facial expressions within the HMD. However, currently-available commercial HMDs would need to be modified to incorporate the specialized optical or piezoelectric sensors. Expression data gathered from within the HMD can be combined with images of the user captured by external cameras to model user expressions, but this approach also requires combining a conventional HMD with additional hardware such as an external camera.

At least in part to address these drawbacks in the conventional practice, a processing system can be trained to label expressions from a set of user expressions associated with a corresponding set of emotions using images (or other sensor streams such as proximity sensors) representative of a portion of a user's face captured by eye tracking sensors integrated in an HMD that occludes the portion of the user's face. In some embodiments, a machine learnt model predicts labels of expressions (or action units) of the user in the image captured by the eye tracking sensors. For example, a convolutional neural network (CNN) algorithm can be trained to identify labels of expressions in a live image of the user from a set including anger, closed eyes, happiness, neutral, and surprise. For another example, the CNN algorithm can be trained to identify labels of action units from a set including brow lower, upper lid raise, cheek raise, eyes closed, left brow raise, left wink, neutral, right brow raise, right wink, and squint. The action units used to determine the current expression of the user correspond to muscle groups that are visible to the eye trackers implemented in the HMD. Action units for muscle groups that are not visible to the eye tracking sensors, e.g., muscle groups in the forehead region or in the mouth/jaw region, are not used to determine the current expression of the user.

To train the machine learnt model, eye-tracking sensors acquire images from a wide variety of individuals while the users are wearing an HMD that incorporates one or more eye tracking sensors. By requesting that the individuals evince certain action units or expressions (which consist of ensembles of action units) while data are being collected for each individual in the group, a correspondence is established between the images of the individuals in the group training data (the eye-tracking camera images) and the labels (the action unit or expression). Supervised learning is used to train the machine learnt model to predict labels for other acquired images based on the established correspondence. Some embodiments of the machine learnt model are trained to predict labels solely on the basis of an image of the eye region of the user. For example, a subsequently acquired (or live) image can be provided as input to the machine learnt model, which then generates a predicted label in response to the input. Some embodiments of the machine learnt model are "personalized" by training the machine learnt model to predict a label for an image of the user based on the live image and a small set of personalization images corresponding to a subset of expressions that are captured when the user wears the headset for first time. For example, the machine learnt algorithm can be trained to subtract a mean neutral image of the user from the eye-tracker images and then identify the label on the basis of the modified eye tracker images. The mean neutral image is constructed based on images acquired while the user has been instructed to maintain a neutral emotion or a set of predetermined emotions. The machine learnt model can also be trained to predict labels for an image of the user based on other combinations of personalization images such as images of the user evincing a neutral expression, a surprised expression, and an angry expression.

Once trained, the machine learnt algorithm can identify a current expression of a user from a live input stream of images acquired by eye tracking sensors in the HMD worn by the user. For example, the machine learnt algorithm can generate labels of predicted expressions (or action units) for the user in each image of a video stream based solely on the input image captured by an eye tracking sensor. If the machine learnt algorithm is personalized, the machine learnt algorithm uses the images acquired from the live input stream and previously acquired personalization images of the user to identify the current expression of the user. During an initialization procedure for the HMD, the user is instructed to evince a series of expressions when the user first puts on the HMD and the eye tracking sensor captures the personalization images while the user is evincing the expressions. The captured personalization images (or combinations or subset thereof) are then provided as additional inputs to the machine learnt algorithm, which uses the input in combination with the live stream of images to predict labels of the expressions of the user in the images. For example, a mean neutral image of the user can be subtracted from the acquired images before identifying labels of expressions or action units in the modified images from the live stream. In some embodiments, the current expression is used to modify a representation of a 3-D model of the user's face or an avatar representative of the user to reflect the current expression. In some embodiments, the expressions that are inferred by the machine learnt algorithm are used to evaluate the effectiveness of VR content in eliciting a desired emotional response, adapt interactive content to the current user emotional state, learn user behavior model to inform creation of new VR content, and the like.

FIG. 1 is a diagram illustrating a processing system 100 that is configured to infer labels of emotions corresponding to facial expressions of the user 105 according to some embodiments. The processing system 100 includes a head mounted device (HMD) 110 that is worn by the user 105 and used to provide virtual reality (VR), augmented reality (AR), or mixed reality (MR) content to the user 105. One or more eye tracking sensors 115 are integrated in the HMD 110 so that the eye tracking sensors 115 are able to track the eyes of the user 105 while the user is wearing the HMD 110. Some embodiments of the eye tracking sensors 115 are able to measure eye positions or eye movement by extracting the eye position and orientation from images in a video stream captured by the eye tracking sensors 115. For example, the eye tracking sensors 115 can include an infrared light source to generate light that is reflected from the eye and sensed by a corresponding sensor in the eye tracking sensors 115 to generate images of the eye, which are then analyzed to determine the position and orientation of the eye gaze. Some embodiments of the HMD 110 integrate other sensors such as proximity sensors.

The processing system 100 also includes a processor 120 and a memory 125. The processor 120 is configured to execute instructions, such as instructions stored in the memory 125 and store the results of the instructions in the memory 125. The processor 120 is also configured to communicate with the HMD 110 over a communication link 130, which can be implemented as a wired connection, a wireless connection, or a combination thereof. The processor 120 can provide information over the link 130 such as values of pixels used to display the VR, AR, or MR images at the HMD. The processor 120 can also receive information over the link 130 such as images captured by the eye tracking sensors 115. The processor 120 can then store the received information in the memory 125. The processor 120 is also configured to render images based on the information received from the HMD 110 or information accessed from the memory 125. The images are rendered on a display 135. Although the display 135 is depicted as a television screen or a monitor in the interest of clarity, some embodiments of the display are implemented in other devices such as cell phones, tablet computers, head mounted displays (HMDs), and the like.

The memory 125 is used to store information representative of a machine learnt algorithm 140 that is used to identify expressions or emotions in images of the user 105 captured by the eye tracking sensors 115. Some embodiments of the machine learnt algorithm 140 are implemented as a convolutional neural network (CNN) algorithm. The machine learnt algorithm 140 is trained to infer labels of expressions of the user 105 using images of other users that are captured concurrently with the other users evincing a predetermined set of expressions associated with emotions such as anger, closed eyes, happiness, neutral, and surprise. For example, the other users can be told to mimic the predetermined set of expressions while wearing an HMD such as the HMD 110. For another example, the other users can be shown images of the predetermined set of expressions and then asked to mimic the expressions while wearing an HMD such as the HMD 110. An eye tracking sensor such as the eye tracking sensors 115 shown in FIG. 1 captures the images concurrently with the user evincing the predetermined set of expressions. The machine learnt algorithm 140 is then trained to predict labels of the emotions based on the established correspondence between the images of the users and the emotions being expressed by the users in those images.

In some embodiments, the machine learnt algorithm 140 is "personalized" based on subsets of the images of the other users. For example, the machine learnt algorithm 140 can "learn" to improve the accuracy of the predicted labels of the emotions of a particular user by combining the subsets of the images of the other users with a subset of the images of the particular user. One example of a subset is a subset of the images that include images of the particular user while evincing a neutral expression. The neutral expression images can then be averaged (e.g., by averaging corresponding pixel values in the images) to define a mean neutral expression for the particular user. The machine learnt algorithm 140 can improve the accuracy of the predicted label of the emotion and an image of the particular user by subtracting the mean neutral image from the image of the particular user and then predicting the label on the basis of the modified image. For example, input (P(I)) to the machine learnt algorithm 140 can be derived from:

$$P(I) = I - \frac{1}{|N_u|} \sum_{I_u \in N_u} I_u$$

where I is the original image for the user (u) and N is the set of neutral images for the user. Other subsets can also be used instead of or in addition to the set of neutral images. The subsets can be predetermined (e.g., by an engineer) or the subsets can be determined by the machine learnt algorithm 140 during the training process.

The trained machine learnt algorithm 140 is then used to infer labels of the expressions of the user 110 based on images captured by the eye tracking sensors 115 while the user 105 is wearing the HMD 110. Some embodiments of the machine learnt algorithm 140 are trained as a variant of the Inception architecture using the TensorFlow library. For example, the machine learnt algorithm 140 can be trained using a predetermined learning rate that decays stepwise by a predetermined step value for every epoch. To prevent overfitting, an aggressive L2 weight decay can be selected. A softmax cross-entropy function can be used as the loss along with L2 regularization:

$$L(w) = -\frac{1}{N} \sum_{n=1}^{N} \sum_{c=1}^{C} [y_c^n \log \hat{y}_n^c - (1 - y_c^n)\log(1 - \hat{y}_n^c)] + \frac{\lambda}{N} \sum_w w^2$$

where N is the number of samples, C are the classes, $y_c^n$ and $\hat{y}_n^c$ are respectively the ground-truth label and softmax activation of the $c^{th}$ class for the $n^{th}$ sample, and w are the network weights.

Some embodiments of the HMD 110 provide information representative of the images captured by the eye tracking sensors 115 over the link 130 to the processor 120. For example, the images can be part of a live video stream of images captured in real-time by the eye tracking sensors 115. The information received over the link 130 can be stored in the memory 125. Some embodiments of the machine learnt algorithm 140 compare values of parameters derived from the images of the user 110 with values of parameters that indicate facial deformations corresponding to the predetermined set of expressions. For example, values of action units derived from the images can be compared with values of action units (or ranges of values) that are associated with each expression in the predetermined set. The machine learnt algorithm 140 identifies one expression from the predetermined set that produces a best match between the values of the parameters derived from the image of the user 110 and the values of the parameters that indicate the facial deformation corresponding to the identified expression. Some embodiments of the parameters are action units associated with a portion of the face of the user 110 that is visible to the eye tracking sensors 115. For example, the parameters can include action units from a set including brow lower, upper lid raise, cheek raise, eyes closed, left brow raise, left wink, neutral, right brow raise, right wink, and squint. The values of the action units indicate degrees of each characteristic, e.g., a large value of the brow lower action unit indicates that the brow is more lowered (relative to a neutral expression) and a small value of the brow lower action unit indicates that the brow is less lowered (relative to the neutral expression).

If the machine learnt algorithm 140 has been personalized, the user 105 is asked to evince a subset of the predetermined set of expressions, such as a neutral expression, during an initialization procedure for the HMD 110. For example, prior to beginning a VR, AR, or MR session, the user 105 can be asked to evince the subset of expressions that are used to personalize the machine learnt algorithm 140 and the eye tracking sensors 115 can capture images of the user 105 concurrently with evincing the subset of expressions. The personalized images 145 are stored in the memory 125. The machine learnt algorithm 140 can then infer labels of the emotions of the user 105 by combining the personalized images 145 with images captured by the eye tracking sensors 115. For example, the machine learnt algorithm 140 can infer labels of the emotions of the user 105 in a live input image stream by subtracting a mean neutral image from the live images and inferring the labels of the emotions from the modified images. As discussed herein, the machine learnt algorithm 140 can also infer labels of emotions on the basis of personalization images 145 associated with other expressions and using other combinations of the personalization images 145 with the captured images.

Figure 2:
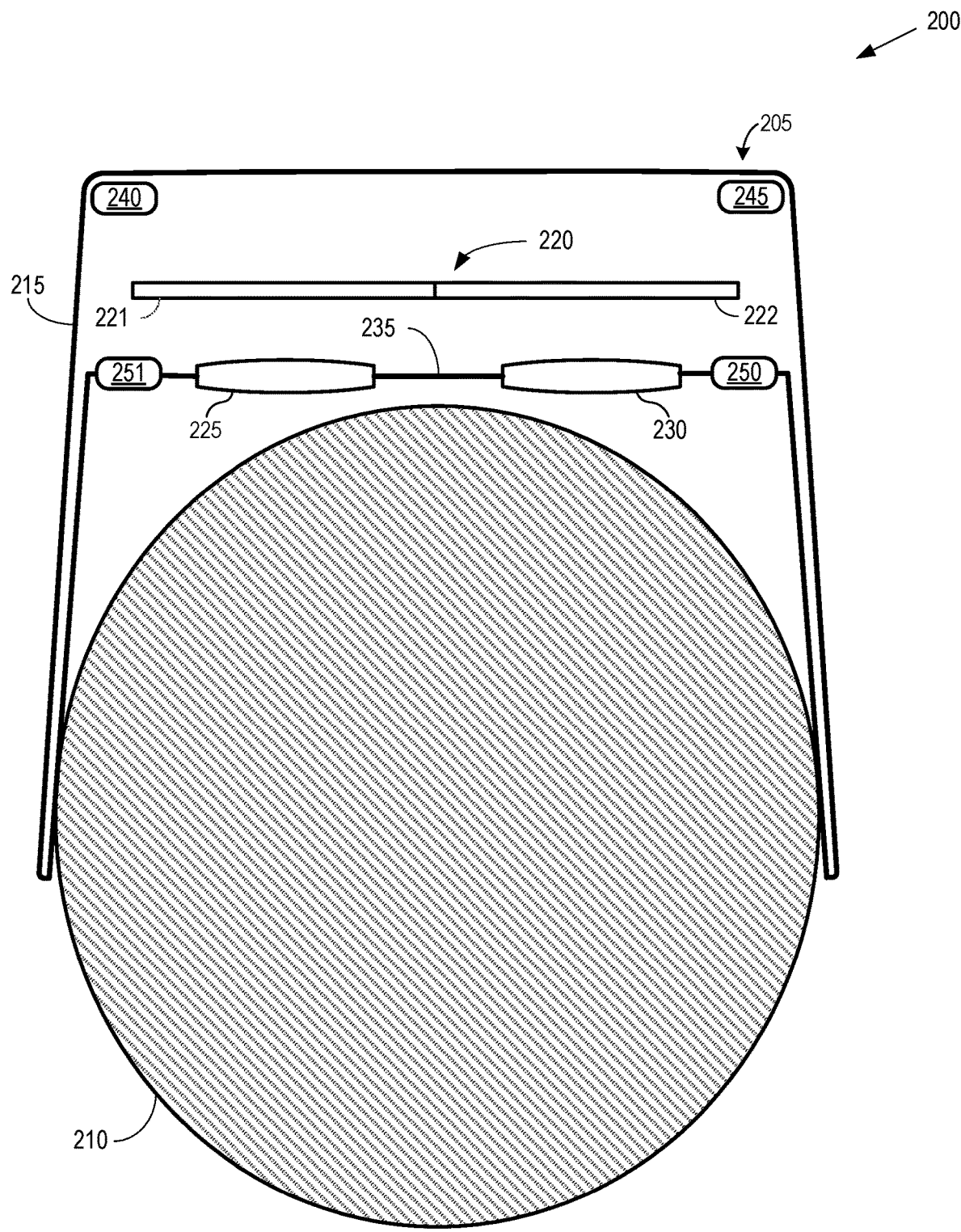
FIG. 2 illustrates a display system that includes an electronic device configured to provide virtual reality (VR), augmented reality (AR), or mixed reality (MR) functionality via a display according to some embodiments.

FIG. 2 illustrates a display system 200 that includes an electronic device 205 configured to provide VR, AR, or MR functionality via a display according to some embodiments. The illustrated embodiment of the electronic device 205 can include a portable user device, such as an HMD, a tablet computer, computing-enabled cellular phone (e.g., a "smartphone"), a notebook computer, a personal digital assistant (PDA), a gaming console system, and the like. In other embodiments, the electronic device 205 can include a fixture device, such as medical imaging equipment, a security imaging sensor system, an industrial robot control system, a drone control system, and the like. For ease of illustration, the electronic device 205 is generally described herein in the example context of an HMD system; however, the electronic device 205 is not limited to these example implementations.

The electronic device 205 is shown in FIG. 2 as being mounted on a head 210 of a user. The electronic device 205 is therefore used to implement some embodiments of the HMD 110 shown in FIG. 1. As illustrated, the electronic device 205 includes a housing 215 that includes a display 220 that generates an image for presentation to the user. In the illustrated embodiment, the display 220 is formed of a left display 221 and a right display 222 that are used to display stereoscopic images to corresponding left eye and right eye. However, in other embodiments, the display 220 is a single monolithic display 220 that generates separate stereoscopic images for display to the left and right eyes. The electronic device 205 also includes eyepiece lenses 225 and 230 disposed in corresponding apertures or other openings in a user-facing surface 235 of the housing 215. The display 220 is disposed distal to the eyepiece lenses 225 and 230 within the housing 215. The eyepiece lens 225 is aligned with the left eye display 221 and the eyepiece lens 230 is aligned with the right eye display 222.

In a stereoscopic display mode, imagery is displayed by the left eye display 221 and viewed by the user's left eye via the eyepiece lens 225. Imagery is concurrently displayed by the right eye display 222 and viewed by the user's right eye via the eyepiece lens 225. The imagery viewed by the left and right eyes is configured to create a stereoscopic view for the user. Some embodiments of the displays 220, 221, 222 are fabricated to include a bezel (not shown in FIG. 2) that encompasses one or more outer edges of the displays 220, 221, 222. In that case, the lenses 225, 230 or other optical devices are used to combine the images produced by the displays 220, 221, 222 so that bezels around the displays 220, 221, 222 are not seen by the user. Instead, lenses 225, 230 merge the images to appear continuous across boundaries between the displays 220, 221, 222.

Some or all of the electronic components that control and support the operation of the display 220 and other components of the electronic device 205 are implemented within the housing 215. Some embodiments of the electronic device 205 include one or more sensors 240, 245 that are used to detect a position or orientation of the electronic device 205. Although two sensors 240, 245 are shown in the interest of clarity, the electronic device 205 can include more or fewer sensors. The sensors 240, 245 can include accelerometers, magnetometers, gyroscopic detectors, position sensors, infrared sensors, and the like, which can be implemented as micro-electrical-mechanical (MEMS) sensors.

The electronic device 205 also implements eye tracking sensors 250, 251 that are configured to track movements and positions of the eyes of the user 210 by measuring the point of gaze of the user 210 or measuring the motion of the eyes relative to the head of the user 210. As discussed herein, some embodiments of the eye tracking sensors 250, 251 implement a non-contact, optical method for measuring eye motion. However, other types of eye trackers can also be used to track movements and positions of the eyes of the user 210. For example, eye motion can be detected using eye attachments such as specially designed contact lenses, electrodes that are placed proximate the eyes, and the like. Some embodiments of the electronic device 205 also implement other sensors such as a proximity sensor that can be used to detect facial deformations. Images captured by the eye tracking sensors 250, 251 are provided to a processing system such as the processing system 100 shown in FIG. 1. For example, a live stream of images captured by the eye tracking sensors 250. 251 while the user 210 is using the electronic device 205 can be provided to a processor, such as the processor 120 shown in FIG. 1, which implements a machine learnt algorithm to infer labels of emotions evinced by the user 105 while wearing the electronic device 205, as discussed herein.

Figure 3:
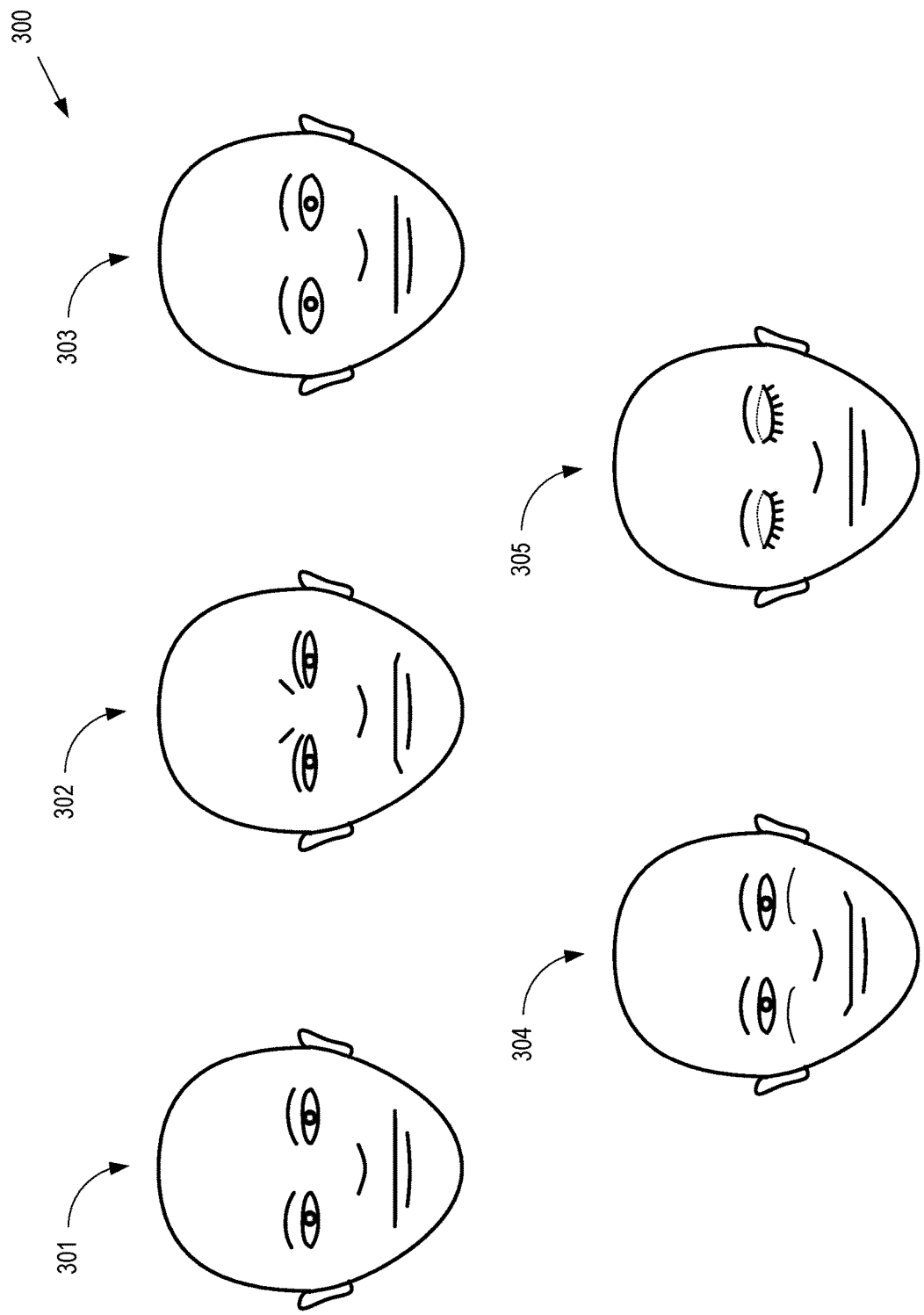
FIG. 3 illustrates a set of facial expressions of a user that can be inferred using a machine learnt algorithm according to some embodiments.

FIG. 3 illustrates a set 300 of facial expressions of a user that can be inferred using a machine learnt algorithm according to some embodiments. The facial expressions include a neutral expression 301, an angry expression 302, a surprised expression 303, a happy expression 304, and a closed-eyes expression 305. The neutral expression 301 is characterized by a neutral eyebrow position, no cheek raise, and a neutral eyelid position (e.g., no raises, winks, or squints). The angry expression 302 is characterized by a lowered eyebrow position, no cheek raise, and narrowed eyelids. The surprised expression 303 is characterized by a raised eyebrow position, no cheek raise, and widened eyelids. The happy expression 304 is characterized by a neutral or slightly lowered eyebrow position, a high degree of cheek raise, and neutral or slightly narrowed eyelids. The closed-eyes expression 304 is characterized by closed eyelids. Additional characteristics of the facial expressions in the set 300, such as measures of other action units, can be used to further characterize the corresponding expressions in some cases.

The expressions 301-305 can be represented by values of parameters that indicate facial deformations of the plurality of first users evincing the plurality of expressions. For example, numerical values can be used to represent values of action units such as eyebrow raises, cheek raises, winks, and squints in the expressions 301-305. A machine learnt algorithm can then infer labels of the expressions that indicate the corresponding emotions by analyzing the numerical values generated from images of the user captured by one or more eye tracking sensors while the user is evincing the expressions 301-305. As discussed herein, eye tracking sensors in an HMD are only able to capture images of portions of the user's face in the region near the user's eyes. Thus, the machine learnt model is trained to infer labels of the expressions 301-305 based on characteristics of the portion of the user's face that is visible to the eye tracking sensors in the HMD. The machine learnt model is not constrained to use any particular set of characteristics, or even characteristics that a human would find sensible, to infer the labels of the expressions 301-305. For example, the machine learnt model can be configured to identify features that are used to infer labels of the expressions 301-305 as part of the machine learning process.

Figure 4:
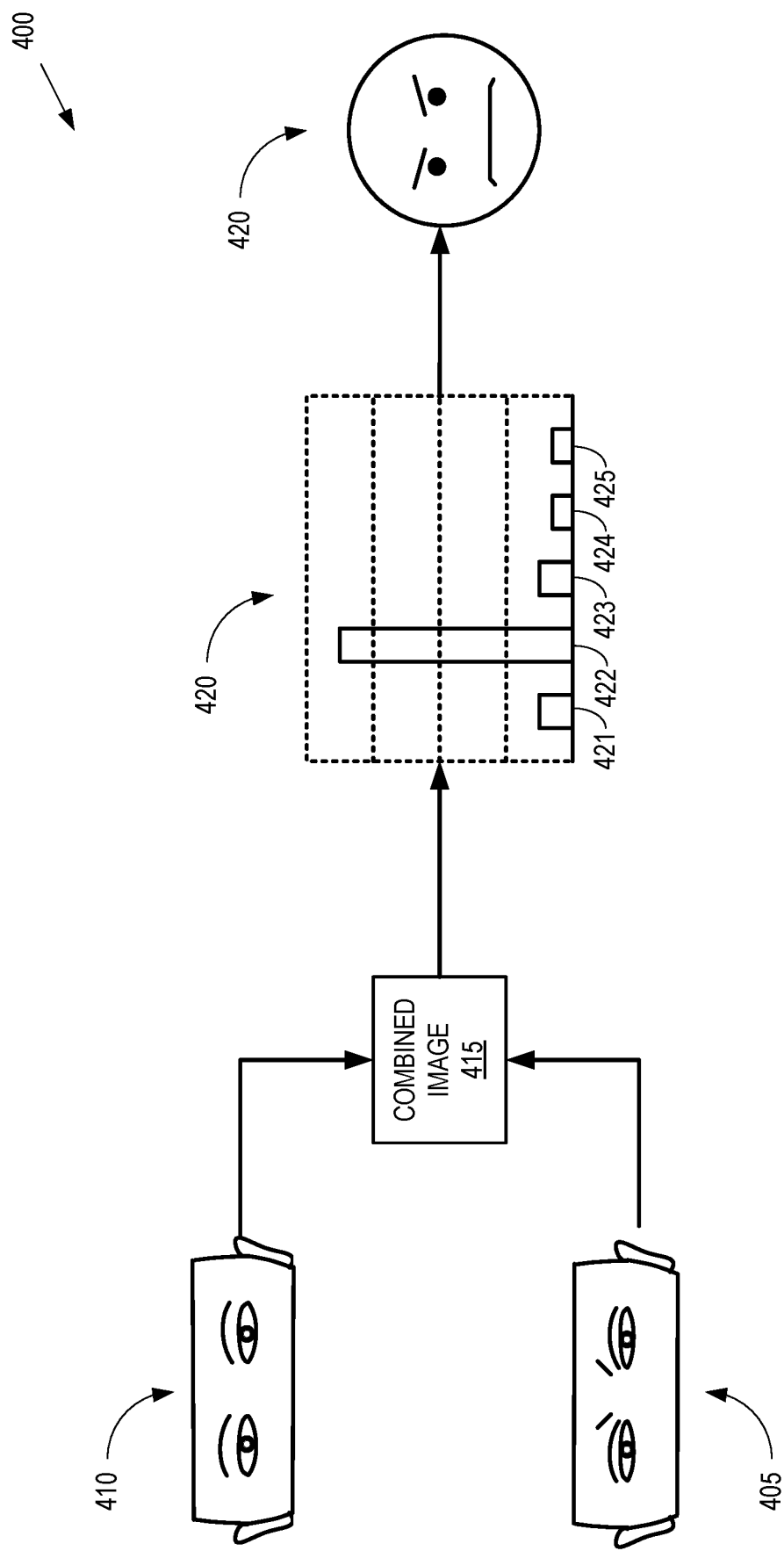
FIG. 4 illustrates a process of inferring a label of an expression based on an image of a portion of the user's face that is visible to eye tracking sensors in an HMD worn by the user according to some embodiments.

FIG. 4 illustrates a process 400 of inferring a label of an expression based on an image of a portion of the user's face that is visible to eye tracking sensors in an HMD worn by the user according to some embodiments. The process 400 is performed by some embodiments of the processing system 100 shown in FIG. 1. An eye tracking sensor such as the eye tracking sensor 115 shown in FIG. 1 captures an image 405 of a portion of the user's face. The process 400 infers the label of the expression shown in the image 405 using a machine learnt algorithm that is trained to infer the labels based on personalization images. For example, the process 400 can infer the label based on a personalization image 410 that represents a mean neutral image of the user. However, some embodiments of the machine learnt algorithm use other personalization images in addition to the personalization image 410. Furthermore, some embodiments of the machine learnt algorithm do not use a personalization image 410 to infer the label of the expression of the user.

The machine learnt algorithm combines the captured image 405 and the personalization image 410 to form a combined image 415. In the illustrated embodiment, the machine learnt algorithm can subtract the personalization image 410 (which in this case is a mean neutral image of the user) from the captured image 405 to form the combined image 415. However, in other embodiments the machine learnt algorithm can use other combinations of the captured image 405 with one or more personalization images 410 to generate the combined image 415. As discussed herein, the combinations can be predetermined or the combinations can be chosen by the machine learnt algorithm. For example, the machine learnt algorithm can generate (positive or negative) weights that are applied to a neutral image, a happy image, and an angry image of the user to generate a personalization image 410 that is then combined with the captured image 405 to form the combined image 415.

A distribution 420 of probabilities of different expressions is generated by the machine learnt algorithm. For example, the distribution 420 indicates a probability 421 that the image of the user indicates a neutral expression, a probability 422 that the image indicates an angry expression, a probability 423 that the image indicates an eyes-closed expression, a probability 424 that the image indicates a happy expression, and a probability 425 that the image indicates a surprised expression. The probabilities of the different expressions can be determined by comparing values of parameters derived from the combined image 415 (such as action units that indicate facial deformations) with corresponding values of the parameters that have been learned by the machine learnt algorithm during the training procedure. In the illustrated embodiment, the probability 422 is larger than any of the other probabilities 421, 423, 424, 425. The angry expression therefore corresponds to a best match between the values of the parameters derived from the combined image 415 and the values of the parameters that indicate the facial deformations corresponding to an angry expression. The machine learnt algorithm therefore infers that the expression in the image 405 is labeled as an angry expression.

In some embodiments, the inferred label of the expression is used to modify a representation of the user to reflect the current expression. For example, the user can be represented by an avatar 430, which is given an angry expression to reflect the angry expression inferred by the machine learnt algorithm from the image 405 captured by the eye tracking sensor. For another example, a 3-D model of the user's face can be modified based on the inferred label to reflect the most likely emotion of the user. In some embodiments, the expressions that are inferred by the machine learnt algorithm are used to evaluate the effectiveness of VR, AR, or MR content in eliciting a desired emotional response, adapt interactive content to the current user emotional state, learn user behavior model to inform creation of new VR, AR, or MR content, and the like.

Figure 5:
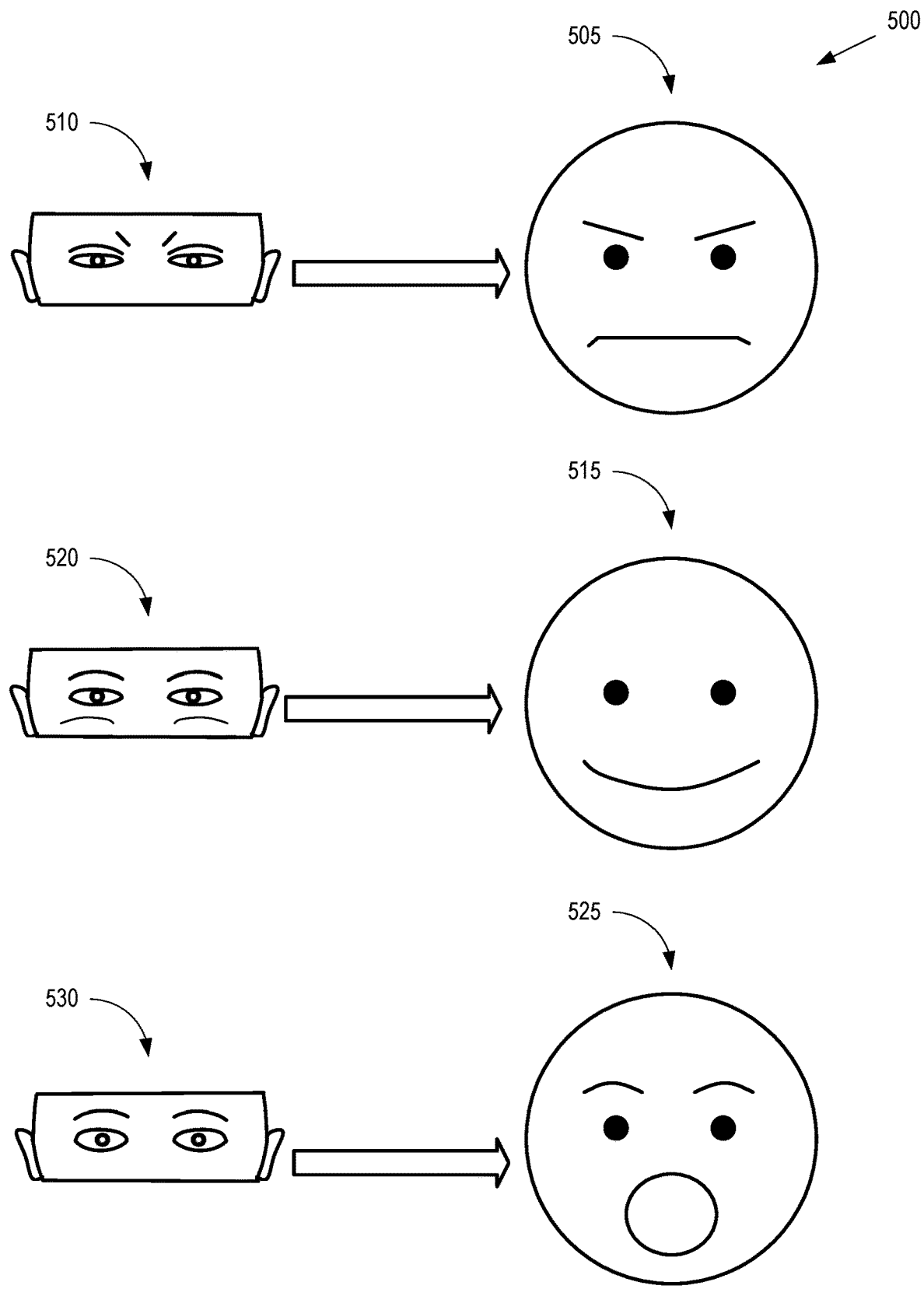
FIG. 5 illustrates a set of avatars that are modified to reflect an inferred expression of the user according to some embodiments.

FIG. 5 illustrates a set 500 of avatars that are modified to reflect an inferred expression of the user according to some embodiments. The expressions of the user can be inferred from images captured by an eye tracking sensor using some embodiments of the processing system 100 shown in FIG. 1 and the process 400 shown in FIG. 4. For example, the avatar 505 is modified to present an angry expression that corresponds to a label of an angry expression inferred by a machine learnt algorithm from the image 510 of the user. For another example, the avatar 515 is modified to present a happy expression that corresponds to a label of a happy expression inferred by the machine learnt algorithm from the image 520 of the user. For another example, the avatar 525 is modified to present a surprised expression that corresponds to a label of a surprised expression inferred by the machine learnt algorithm from the image 530 of the user.

Figure 6:
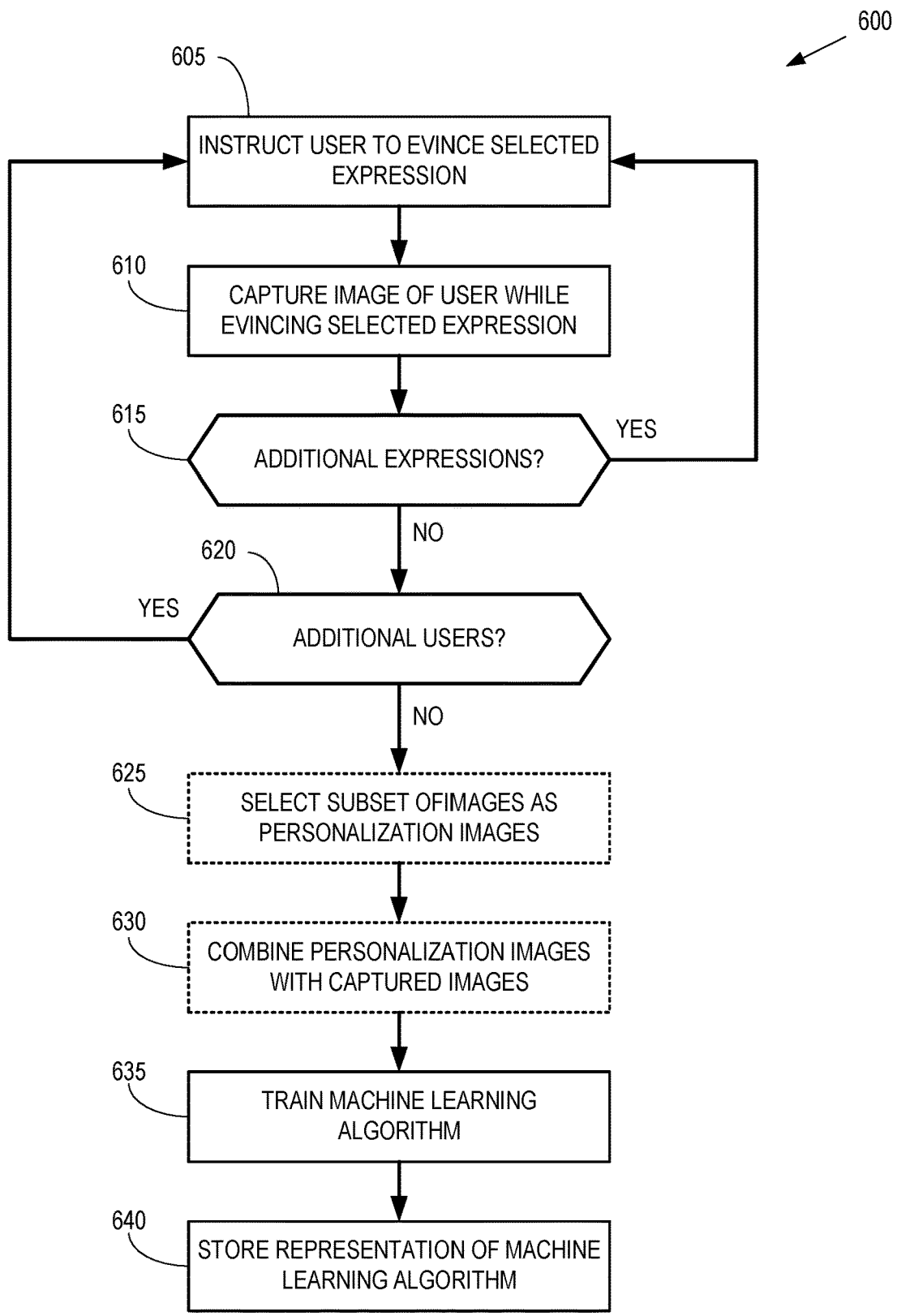
FIG. 6 is a flow diagram of a method of training a machine learnt algorithm to infer labels of expressions in images of one or more users captured by an eye tracking sensor according to some embodiments.

FIG. 6 is a flow diagram of a method 600 of training a machine learnt algorithm to infer labels of expressions in images of one or more users captured by an eye tracking sensor according to some embodiments. The method 600 is implemented in some embodiments of the processing system 100 shown in FIG. 1. Training is performed based on images captured by one or more eye tracking sensors (or other sensors such as proximity sensors) integrated in an HMD worn by one or more users.

At block 605, a user is instructed to evince a selected expression from a set of expressions that includes expressions such as a neutral expression, a happy expression, an angry expression, a surprised expression, and eyes-closed expression, and the like. The instructions can be provided in written form, in spoken form, or using images that illustrate the expressions. At block 610, the eye tracking sensors capture an image of the user concurrently with the user evincing the selected expression. In some cases, not all of the users are able to evince all of the expressions in the set of expressions. For example, not everyone is able to do a right brow raise or a left brow raise. Some expressions may therefore be bypassed for some users. However, the machine learnt algorithm can be effectively trained even in cases where some of the users do not evince all of the expressions in the set of expressions.

At decision block 615, the system determines whether there are additional expressions in the set. If so, the method 600 flows to block 605 and the user is instructed to evince another expression from the set. If not and the user has evinced all of the expressions in the set during the capture process, the method 600 flows to decision block 620.

At decision block 620, the system determines whether there are additional users in the group of users that are used to train the machine learnt algorithm. If so, the method 600 flows to block 605 and the next user is instructed to evince an expression selected from the set. If not, the method flows to block 625. Although the method 600 is used to capture images of a sequence of users wearing the same HMD during subsequent time intervals, this is not required in all embodiments of the method 600. For example, images of multiple users evincing the set of expressions can be captured using multiple HMDs worn by the multiple users. Images of the multiple users wearing the different HMDs can be captured during different time intervals or concurrently.

At block 625, a subset of the images of the users is selected and used to personalize the machine learnt algorithm. For example, neutral images of each of the users can be selected and used to generate a mean neutral image. As discussed herein, the images can be predetermined or selected as part of the supervised learning process that is used to train the machine learnt algorithm. The block 625 is optional (as indicated by the dotted line box) and is not required to train embodiments of the machine learnt algorithm that do not implement personalization.

At block 630, the personalization images for each of the users in the group of users are combined with the other captured images to form personalized data sets for each of the users in the group. For example, mean neutral images for each of the users in the group can be subtracted from the captured images to form a personalized data set for each of the users. As discussed herein, other combinations of the subset of images can be used to form the personalization images for each user. The block 630 is optional (as indicated by the dotted line box) and is not required to train embodiments of the machine learnt algorithm that do not implement personalization.

At block 635, supervised learning is used to train the machine learnt algorithm to infer labels of expressions in captured images of the users. In the interest of clarity, the blocks 625, 630, 635 are depicted as sequential steps in the method 600. However, supervised learning of some embodiments of the machine learnt algorithm includes selecting the subset of images that form the personalization images, determining the combinations of the personalization images and captured images that are used to infer the labels of the expressions, and then training the machine learnt algorithm to infer the labels on the basis of the identify combinations of the personalization images.

At block 640, a representation of the machine learnt algorithm is stored in a non-transitory computer readable medium, such as the memory 125 shown in FIG. 1.

Figure 7:
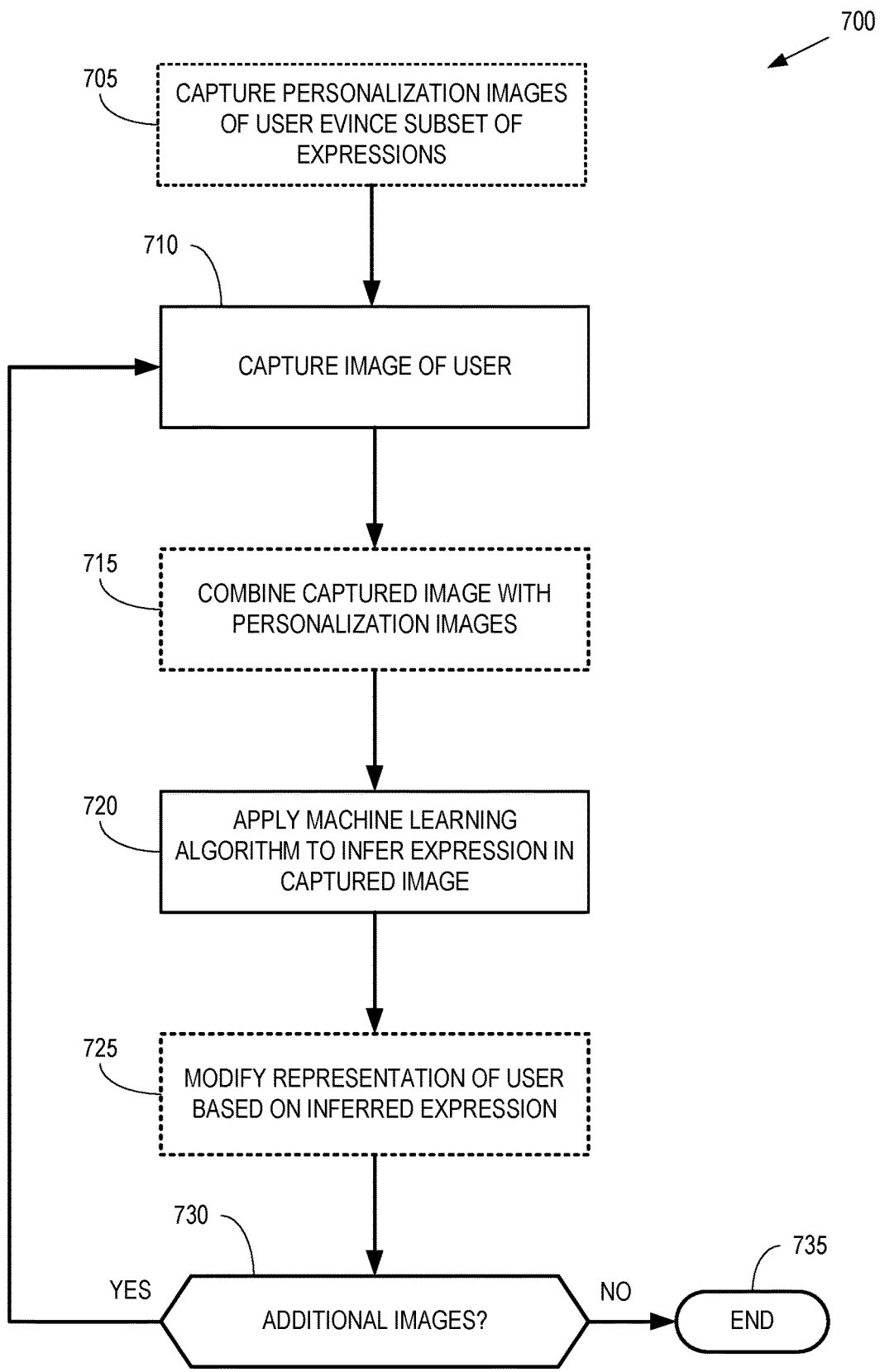
FIG. 7 is a flow diagram of a method of inferring labels of expressions in images of a user captured by one or more eye tracking sensors integrated in an HMD according to some embodiments.

FIG. 7 is a flow diagram of a method 700 of inferring labels of expressions in images of a user captured by one or more eye tracking sensors integrated in an HMD according to some embodiments. The method 700 is implemented in some embodiments of the processing system 100 shown in FIG. 1. For example, the method 700 can be implemented using a processor such as some embodiments of the processor 120 shown in FIG. 1.

At block 705, the user is asked to evince a subset of expressions and the one or more eye tracking sensors in the HMD capture images of the user concurrently with the user evincing the subset. For example, the HMD can be used to display pictures representing the subset of expressions and the user can be instructed to evince the corresponding expressions of the eye tracking sensors capture images of the user. Capture of the personalization images at block 705 can be performed during an initialization procedure that is performed the first time the user puts on the HMD. The block 705 is optional (as indicated by the dotted line box) and is not required in embodiments that do not implement personalization.

At block 710, an image of the user is captured by the one or more eye tracking sensors. For example, the eye tracking sensors can capture an image that is part of a live stream of images representative of a portion of the user's face that is visible to the eye tracking sensors from within the HMD while the user is wearing the HMD. The captured image is stored or otherwise made available to the processor for subsequent processing.

At block 715, the processor combines the captured image with the personalization image. For example, the processor can subtract a mean neutral image from the captured image, as discussed herein. The block 715 is optional (as indicated by the dotted line box) and is not required in embodiments that do not implement personalization.

At block 720, the processor applies a machine learnt algorithm to infer a label of an expression of the user in the captured image. If personalization is implemented, the machine learnt algorithm infers the label of the expression on the basis of the modified image formed by combining the captured image with the personalization image. For example, the machine learnt algorithm can infer a label indicating a neutral expression, and anger expression, a happy expression, a surprised expression, a close-eyes expression, and the like. Some embodiments of the machine learnt algorithm are trained according to the method 600 shown in FIG. 6.

At block 725, the processor modifies a representation of the user based on the inferred label of the expression in the captured image. For example, the processor can modify an avatar of the user to represent an emotion corresponding to the inferred label. The block 725 is optional (as indicated by the dotted line box) and is not required in all embodiments of the method 700. For example, the inferred label of the expression can be used for other purposes such as evaluating effectiveness of content viewed by the user wearing the HMD in eliciting a desired emotional response, adapting interactive content viewed by the user wearing the HMD based on the inferred label, and generating a user behavior model to inform creation of content for viewing by the user wearing the HMDs.

At decision block 730, the processor determines whether there are additional images to process. For example, if the processor is inferring labels of expressions in a live stream of images, the processor can determine that the next image has arrived from the eye tracking sensors for processing. If so, the method 700 flows to block 710. If not, the method 700 flows to block 735 and the method 700 ends.

In some embodiments, certain aspects of the techniques described above may implemented by one or more processors of a processing system executing software. The software comprises one or more sets of executable instructions stored or otherwise tangibly embodied on a non-transitory computer readable storage medium. The software can include the instructions and certain data that, when executed by the one or more processors, manipulate the one or more processors to perform one or more aspects of the techniques described above. The non-transitory computer readable storage medium can include, for example, a magnetic or optical disk storage device, solid state storage devices such as Flash memory, a cache, random access memory (RAM) or other non-volatile memory device or devices, and the like. The executable instructions stored on the non-transitory computer readable storage medium may be in source code, assembly language code, object code, or other instruction format that is interpreted or otherwise executable by one or more processors.

A computer readable storage medium may include any storage medium, or combination of storage media, accessible by a computer system during use to provide instructions and/or data to the computer system. Such storage media can include, but is not limited to, optical media (e.g., compact disc (CD), digital versatile disc (DVD), Blu-Ray disc), magnetic media (e.g., floppy disc, magnetic tape, or magnetic hard drive), volatile memory (e.g., random access memory (RAM) or cache), non-volatile memory (e.g., read-only memory (ROM) or Flash memory), or microelectromechanical systems (MEMS)-based storage media. The computer readable storage medium may be embedded in the computing system (e.g., system RAM or ROM), fixedly attached to the computing system (e.g., a magnetic hard drive), removably attached to the computing system (e.g., an optical disc or Universal Serial Bus (USB)-based Flash memory), or coupled to the computer system via a wired or wireless network (e.g., network accessible storage (NAS)).

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. Moreover, the particular embodiments disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular embodiments disclosed above may be altered or modified and all such variations are considered within the scope of the disclosed subject matter. Accordingly, the protection sought herein is as set forth in the claims below.

What is claimed is:

1. A method comprising:
forming at least one personalization image of a first user evincing a plurality of expressions by:
calculating a mean neutral image of the first user by averaging corresponding pixel values of images of the first user, wherein the images of the first user comprise the first user evincing one or more neutral expressions, and wherein the at least one personalization image includes the mean neutral image;
capturing a first image of the first user using an eye tracking sensor implemented in a head mounted device (HMD) worn by the first user; and
inferring a label of an expression evinced by the first user in the first image using a machine learnt algorithm trained to predict a label for an image of the first user based on a live image of the first user and the at least one personalization image of the first user.

2. The method of claim 1, wherein the machine learnt algorithm comprises a convolutional neural network algorithm.

3. The method of claim 1, wherein the machine learnt algorithm is trained using second images of a plurality of second users concurrently with the plurality of second users evincing the plurality of expressions, wherein the plurality of expressions correspond to values of parameters that indicate facial deformations of the plurality of second users evincing the plurality of expressions.

4. The method of claim 3, wherein inferring the label of the expression evinced by the first user comprises comparing values of the parameters derived from the first image with the values of the parameters that indicate the facial deformations corresponding to the plurality of expressions.

5. The method of claim 4, wherein inferring the label of the expression evinced by the first user comprises identifying one of the plurality of expressions that corresponds to a best match between the values of the parameters derived from the first image and the values of the parameters that indicate the facial deformation corresponding to the identified one of the plurality of expressions.

6. The method of claim 4, wherein the values of the parameters comprise values of action units that indicate states of muscle contraction in independent muscle groups on respective faces of the plurality of second users.

7. The method of claim 1, further comprising:
combining the at least one personalization image with the first image to form a modified first image; and
inferring the label of the expression evinced by the first user in the first image by applying the machine learnt algorithm to the modified first image.

8. The method of claim 7, wherein the machine learnt algorithm is trained to predict the labels based on a subset of the plurality of expressions.

9. The method of claim 8, wherein combining the at least one personalization image with the first image comprises generating the mean neutral image of the first user using the at least one personalization image and subtracting the mean neutral image from the first image.

10. The method of claim 1, further comprising:
modifying at least one of a representation of a three-dimensional (3-D) model of a face of the first user or an avatar representative of the first user based on the inferred label of the expression.

11. The method of claim 1, further comprising:
utilizing the inferred label of the expression to perform at least one of evaluating effectiveness of content viewed by the first user wearing the HMD in eliciting a desired emotional response, adapting interactive content viewed by the first user wearing the HMD based on the inferred label of the expression, and generating a user behavior model to inform creation of content for viewing by the first user wearing the HMD.

12. A method comprising:
forming at least one personalization image of a first user evincing a plurality of expressions by:
calculating a mean neutral image of the first user by averaging corresponding pixel values of images of the first user, wherein the images of the first user comprise the first user evincing one or more neutral expressions, and wherein the at least one personalization image includes the mean neutral image;
capturing a first image of the first user using an eye tracking sensor implemented in a head mounted device (HMD); and
inferring a label of an expression evinced by the first user in the first image using a machine learnt algorithm trained to predict labels of a plurality of expressions using a plurality of images of a plurality of users evincing the plurality of expressions and a plurality of personalization images of the plurality of users, each personalization image of the plurality of personalization images being the mean neutral image of a corresponding user of the plurality of users.

13. The method of claim 12, further comprising:
generating a modified image by combining the first image with the first personalization image of the plurality of personalization images, the first personalization image corresponding to the mean neutral image of the first user, wherein the label of the expression evinced by the first user in the first image is inferred using the machine learnt algorithm based on the modified image.

14. The method of claim 13, wherein combining the first image with the first personalization image comprises:
subtracting the mean neutral image from the first image.

15. The method of claim 12, wherein the first image depicts only a portion of a face of the first user, the portion being proximal to one or both eyes of the first user.

16. A system comprising:
head mounted device (HMD) comprising:
an eye tracking sensor configured to a first image of a first user; and
a processor configured to execute computer-readable instructions that, when executed, cause the processor to:
form at least one personalization image of the first user evincing a plurality of expressions by:
calculating a mean neutral image of the first user by averaging corresponding pixel values of images of the first user, wherein the images of the first user comprise the images of the first user, and wherein the at least one personalization image includes the mean neutral image; and
infer a label of an expression evinced by the first user in the first image using a machine learnt algorithm trained to predict labels of the plurality of expressions using a plurality of images of a plurality of users evincing the plurality of expressions and a plurality of personalization images of the plurality of users, each personalization image of the plurality of personalization images being a mean neutral image of a corresponding user of the plurality of users.

17. The system of claim 16, wherein the computer-readable instructions, when executed, further cause the processor to:
   generate a modified image by combining the first image with a first personalization image of the plurality of personalization images, the first personalization image corresponding to the mean neutral image of the first user, wherein the label of the expression evinced by the first user in the first image is inferred using the machine learnt algorithm based on the modified image.

18. The system of claim 17, wherein combining the first image with the first personalization image comprises:
   subtracting the mean neutral image from the first image.

19. The system of claim 16, wherein the first image depicts only a portion of a face of the first user, the portion being proximal to one or both eyes of the first user.

20. The system of claim 16, wherein the computer-readable instructions, when executed, further cause the processor to:
   modify a computer-generated representation of the first user to represent an emotion corresponding to the label inferred using the machine learnt algorithm.

* * * * *